US00PP18972P2

(12) United States Plant Patent
Hanes

(10) Patent No.: US PP18,972 P2
(45) Date of Patent: Jun. 24, 2008

(54) *VERBENA* PLANT NAMED 'LAN UPPURMOS'

(50) Latin Name: *Verbena hybrida*
Varietal Denomination: Lan Uppurmos

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/709,637

(22) Filed: Feb. 22, 2007

(51) Int. Cl.
*A01H 5/00* (2006.01)

(52) U.S. Cl. ..... Plt./308
(58) Field of Classification Search ..... Plt./308
See application file for complete search history.

*Primary Examiner*—Kent Bell
(74) *Attorney, Agent, or Firm*—Jondle & Associates, P.C.

(57) ABSTRACT

A *verbena* cultivar particularly distinguished by its violet-purple colored flowers with a white background, vigorous, free-branching with multiple secondary lateral branches, upright growth habit becoming slightly spreading and decumbant, and tolerance to powdery mildew is disclosed.

1 Drawing Sheet

Figure 1:
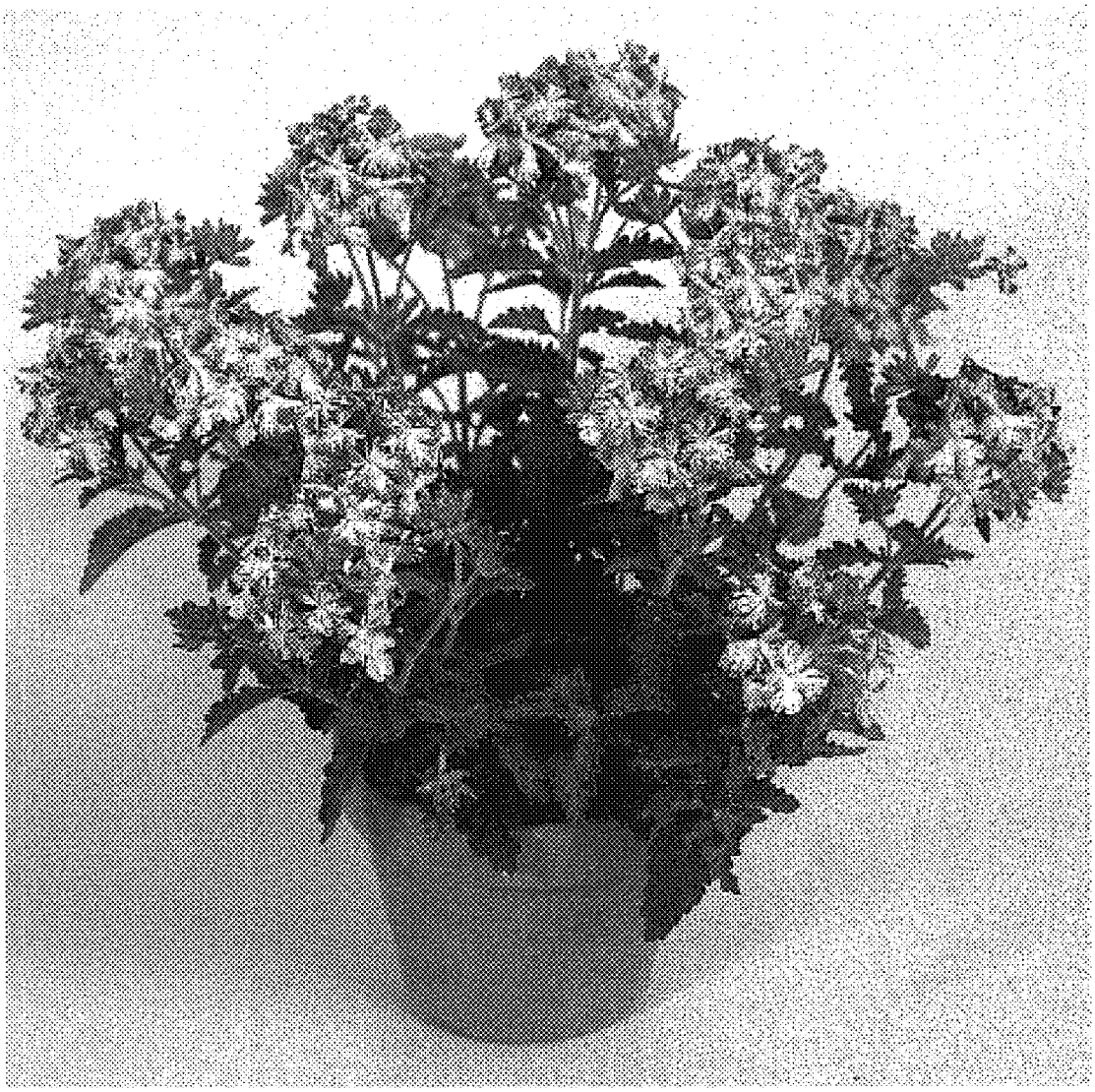

Genus and species: *Verbena hybrida.*
Variety denomination: 'Lan Uppurmos'.

BACKGROUND OF THE NEW PLANT

The present invention comprises a new and distinct cultivar of *verbena,* botanically known as *Verbena hybrida,* and hereinafter referred to by the cultivar name 'Lan Uppurmos'. The new cultivar originated in 2003 in Gilroy, Calif. from the sib (two unnamed sister line cross) cross of '1773', an unpatented purple mosaic flowered proprietary *verbena*.

The seeds produced by the pollination were sown in June 2004. A single plant selection was chosen for further evaluation and for asexual propagation in September 2004.

The new cultivar was created in 2004 in Gilroy, Calif. and has been asexually reproduced repeatedly by vegetative cuttings and tissue culture in Gilroy, Calif. and Andijk, The Netherlands over a two-year period. The plant has also been trialed at Gilroy, Calif., Andijk, The Netherlands and Hillscheid, Germany. The present invention has been found to retain its distinctive characteristics through successive asexual propagations.

Plants Breeder's Rights for this cultivar have been applied for in Switzerland on Oct. 30, 2006.

SUMMARY OF THE INVENTION

The following are the most outstanding and distinguishing characteristics of the new cultivar when grown under normal horticultural practices in Gilroy, Calif. and Andikj, The Netherlands.

1. Violet-purple flower color with a white background;
2. Upright plant growth habit becoming slightly spreading and decumbent plant habit;
3. Vigorous and free branching with multiple secondary lateral branches; and
4. Tolerance to powdery mildew.

DESCRIPTION OF PHOTOGRAPH

This new *verbena* plant is illustrated by the accompanying photograph which shows overall plant habit, including blooms, buds and foliage of 12 to 14 week old plants. The photographs were taken of plants grown in a greenhouse in Hillscheid, Germany in May 2006. The colors shown are as true as can be reasonably obtained by conventional photographic procedures.

DESCRIPTION OF THE NEW CULTIVAR

The following detailed descriptions set forth the distinctive characteristics of 'Lan Uppurmos'. The data which defines these characteristics were collected from asexual reproductions carried out in Gilroy, Calif. The plant history was taken from plants approximately 12-weeks old, grown in 4-inch pots, in Gilroy, Calif. in the fall and winter seasons. The plants had one plant growth regulator treatment and one terminal pinch at the onset of the trial. Color readings were taken in a LEXAN-covered greenhouse in January under natural light. Color references are primarily to the R.H.S. Colour Chart of The Royal Horticultural Society of London (R.H.S.) (2001 edition). Texture description details were observed with a dissecting microscope.

DETAILED BOTANICAL DESCRIPTION

Classification:
*Botanical.—Verbena hybrida.*
*Common name.—Verbena.*

Parentage: Sib (two unnamed sister line cross) cross of '1773' a proprietary *verbena* plant having purple mosaic flowers (unpatented).

Growth:
*Form.*—Herbaceous annual; mostly upright growth in the early stages though semi-compact, then becoming slightly spreading and decumbent.
*Growth and branching habit.*—Vigorous and free-branching with multiple secondary lateral branches.
*Height* (*measured from the top of the soil, including flowers*).—20.0 cm to 25.0 cm.
*Width* (*horizontal plant diameter*).—23.0 cm to 27.0 cm.
*Time to produce a finished flowering plant.*—Approximately 10 weeks for a 12 cm pot in the spring.

*Outdoor plant performance.*—Use in containers and hanging baskets.

*Time to initiate and develop roots.*—Less than 14 days.

*Root description.*—Fibrous, fleshy, white.

Leaves:

*Arrangement.*—Opposite.

*Immature leaf.*—Color: Upper surface: RHS 137B. Lower surface: RHS 138A.

*Mature leaf.*—Color: Upper surface: RHS 137A. Lower surface: RHS 138A. Length: 5.4 cm to 6.7 cm. Width: 3.0 cm to 3.6 cm. Shape: Ovate to lanceolate. Apex: Obtuse to rounded. Base: Attenuate. Margin: Irregular, crenately incised. Texture: Upper surface: Hirsute. Lower surface: Hirsute only on the veins. Venation: Pinnate. Venation color: RHS 144C.

*Petioles.*—Length: 0.4 cm to 0.5 cm. Diameter: 0.2 cm. Color: RHS 144C. Texture: Hirsute.

Stems:

*Number of branches per plant.*—6 to 8 main branches.

*Color.*—RHS 144C.

*Length.*—18.0 cm. to 20.0 cm.

*Diameter* (*measured from the midpoint*).—0.3 cm to 0.35 cm.

*Internode length.*—3.0 cm to 3.5 cm.

*Texture.*—Heavily hirsute; few glandular hairs, some with a violet-purple color.

*Stem anthocyanin.*—Absent.

Flower buds:

*Color* (*at tight bud*).—RHS N155C with small spots of RHS 83A.

*Shape.*—Tubular.

*Diameter.*—0.3 cm.

*Length.*—1.5 cm to 1.8 cm.

Inflorescence:

*Blooming habit.*—Flowers continuously from spring through fall; flowers appear about 9 to 10 weeks after planting of rooted cuttings.

*Lastingness of individual blooms on the plant.*—5 to 7 days.

*Fragrance.*—Absent.

*Inflorescence type.*—Terminal raceme.

*Horizontal diameter of inflorescence.*—5.0 cm to 6.0 cm.

*Vertical diameter of inflorescence.*—2.5 cm to 3.0 cm.

*Number of florets per raceme.*—15 to 20.

*Peduncle.*—Color: RHS 144A. Diameter: 0.15 cm to 0.2 cm. Length: 4.0 cm to 7.0 cm. Texture: Hirsute; pilose; glandular hairs, most with a violet-purple color.

Flowers:

*Floret form.*—Salverform; sessile on spikes.

*Diameter.*—2.5 cm.

*Number of petals and arrangement.*—Each floret is composed of 5 petals fused at the base.

*Immature flower.*—Color: Upper surface: RHS N155C base color with small bars closest to RHS N81A. Lower surface: RHS N155C base color with small bars of RHS N81B.

*Mature flower.*—Color: Upper surface: RHS N155C base color with small bars a little darker than RHS N81A. Bars are 0.1 cm to 0.3 cm in length. Lower surace: RHS N155C base color with small bars of RHS N81B. Corolla: Tube color (inside): RHS N155C. Tube color (outside): RHS N155C. Tube length: 2.0 cm to 2.1 cm.

*Petals.*—Size: Length: 1.1 cm to 1.2 cm. Width: 0.8 cm to 1.1 cm. Lobe shape: Obovate. Apex: Emarginate. Base: Fused. Margin: Entire, wavey, so that flowers are not flat. Texture: Upper surface: Papillose. Lower surface: Pilose; papillose.

*Calyx.*—Sepals: Five sepals whose margins are fused to each other along their length, with a transparent membrane of less than 0.1 cm in width and with one smaller sepal (0.7 cm) attached to the base of the calyx. General color: RHS 143B for the outer surface; inner surface was not observed. Length: 1.1 cm to 1.2 cm. Width: 0.3 cm. Shape: Linear. Apex: Acute. Base: Fused. Margin: Fused. Texture: Pilose, glandular hairs, some with a violet-purple color.

Reproductive organs:

*Stamens.*—Anthers and filaments are fused to the upper half of the corolla tube.

*Anther quantity.*—Four with two pollen sacs per anther.

*Anther length.*—0.1 cm.

*Pollen.*—Amount: Scant to moderate. Color: RHS 5C.

*Pistils.*—1.

*Style length.*—1.5 cm to 1.6 cm.

*Style color.*—RHS 145C.

*Stigma color.*—RHS 146D.

Fruit/Seed set: Have not been produced.

Disease and insect resistance: Tolerant to powdery mildew.

COMPARISON WITH PARENTAL AND COMMERCIAL CULTIVARS

'Lan Uppurmos' differs from the proprietary, sib cross parent '1773' (unpatented) in that 'Lan Uppurmos' has more purple bars in the flower than '1773'. Additionally, 'Lan Uppurmos' has a more compact and upright habit with more vigor than '1773'.

'Lan Uppurmos' differs from the commercial variety 'Kievervlek' (U.S. Plant Pat. No. 14,303) by having a more upright plant habit. 'Lan Uppurmos' has larger and lighter foliage with shorter internodes and peduncles than 'Kievervlek'. Additionally 'Lan Uppurmos' has light violet-purple flowers than 'Kievervlek'.

I claim:

1. A new and distinct cultivar of *verbena* plant as shown and described herein.

* * * * *